US012385910B2

(12) United States Patent
Kaneko et al.

(10) Patent No.: US 12,385,910 B2
(45) Date of Patent: Aug. 12, 2025

(54) SOLID PHASE CARRIER AND KIT

(71) Applicant: FUJIFILM Corporation, Tokyo (JP)

(72) Inventors: Kazuhei Kaneko, Ashigarakami-gun (JP); Yoshinori Kanazawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1123 days.

(21) Appl. No.: 17/162,124

(22) Filed: Jan. 29, 2021

(65) Prior Publication Data

US 2021/0148900 A1    May 20, 2021

Related U.S. Application Data

(63) Continuation of application No. PCT/JP2019/029758, filed on Jul. 30, 2019.

(30) Foreign Application Priority Data

Jul. 31, 2018  (JP) ................. 2018-143131

(51) Int. Cl.
| | | |
|---|---|---|
| *G01N 33/543* | (2006.01) | |
| *C08F 212/08* | (2006.01) | |
| *C08F 220/60* | (2006.01) | |
| *G01N 33/546* | (2006.01) | |
| *G01N 33/58* | (2006.01) | |

(52) U.S. Cl.
CPC ..... *G01N 33/546* (2013.01); *G01N 33/54393* (2013.01); *G01N 33/582* (2013.01)

(58) Field of Classification Search
CPC .......... G01N 33/546; G01N 33/54393; G01N 33/582; G01N 33/54353; C08F 4/34; C08F 212/08; C08F 220/606

See application file for complete search history.

(56) References Cited

U.S. PATENT DOCUMENTS

| | | | |
|---|---|---|---|
| 2006/0035388 A1 | 2/2006 | Yoshinaga et al. | |
| 2006/0147413 A1* | 7/2006 | Alferiev | A61K 31/765 |
| | | | 525/279 |
| 2008/0070319 A1 | 3/2008 | Makino | |
| 2012/0165646 A1 | 6/2012 | Yamauchi et al. | |
| 2013/0011336 A1 | 1/2013 | Niitsu et al. | |
| 2017/0292947 A1 | 10/2017 | Ueya | |
| 2019/0185745 A1 | 6/2019 | Watanabe et al. | |

FOREIGN PATENT DOCUMENTS

| | | | |
|---|---|---|---|
| EP | 3 193 172 A1 | 7/2017 | |
| JP | 2004-157072 A | 6/2004 | |
| JP | 2008-74892 A | 4/2008 | |
| JP | 2012-501963 A | 1/2012 | |
| JP | 2012-149034 A | 8/2012 | |
| WO | WO-0065352 A1 * | 11/2000 | ......... A61B 5/14546 |
| WO | WO 2016/039293 A1 | 3/2016 | |
| WO | WO 2017/215883 A1 | 12/2017 | |
| WO | WO 2018/038138 A1 | 3/2018 | |
| WO | WO 2016/177354 A2 | 11/2018 | |

OTHER PUBLICATIONS

Japanese Notice of Reasons for Refusal for corresponding Japanese Application No. 2020-534652, dated Jan. 18, 2022, with an English translation.
International Preliminary Report on Patentability and Written Opinion of the International Searching Authority with an English translation (forms PCT/IB/373, PCT/ISA/237 and PCT/IB/326), dated Feb. 11, 2021, for corresponding International Application No. PCT/JP2019/029758.
International Search Report (form PCT/ISA/210), dated Nov. 5, 2019, for corresponding International Application No. PCT/JP2019/029758, with an English translation.
Altintas et al., "Methacryloylamidoglutamic acid having porous magentic beads as a stationary phase in metal chelate affinity chromatography," Journal of Biomaterials Science, Polymer Edition, vol. 17, No. 1-2, 2006, pp. 213-226.
Extended European Search Report for corresponding European Application No. 19843594.3, dated Oct. 18, 2021.
Lange et al., "Efficient and Tunable Three-Dimensional Functionalization of Fully Zwitterionic Antifouling Surface Coatings," Langmuir, vol. 32, No. 40, Sep. 30, 2016, pp. 10199-10205.
Lísalová et al., "Ultralow-Fouling Behavior of Biorecognition Coatings Based on Carboxy-Functional Brushes of Zwitterionic Homo- and Copolymers in Blood Plasma: Functionalization Matters," Analytical Chemistry, vol. 89, No. 6, Feb. 24, 2017, pp. 3524-3531.
Luo et al., "Thermo- and pH-Responsive Polymer Derived from Methacrylamide and Aspartic Acid," Macromolecules, vol. 43, No. 19, Sep. 17, 2010, pp. 8101-8108.

* cited by examiner

*Primary Examiner* — Gregory S Emch
*Assistant Examiner* — Nam P Nguyen
(74) *Attorney, Agent, or Firm* — Birch, Stewart, Kolasch & Birch, LLP

(57) ABSTRACT

An object of the present invention is to provide a solid phase carrier for carrying a bioactive substance, which achieves both the high non-specific adsorption inhibitory effect and high ligand binding amount. Another object of the present invention is to provide a kit for measuring a measurement target substance in a biosample, which includes the solid phase carrier. According to an embodiment of the present invention, a solid phase carrier for carrying a bioactive substance is provided which includes a copolymer present on a surface of the solid phase. The copolymer has a structural unit in which a hydrophilic group and a bioactive substance-reactive group are bonded to an acidic amino acid-derived group through a predetermined linking group.

15 Claims, 2 Drawing Sheets

SOLID PHASE CARRIER AND KIT

CROSS-REFERENCE TO RELATED APPLICATIONS

This application is a Continuation of PCT International Application No. PCT/JP2019/029758 filed on Jul. 30, 2019, which claims priority under 35 U.S.C. § 119(a) to Japanese Patent Application No. 2018-143131 filed on Jul. 31, 2018. Each of the above application(s) is hereby expressly incorporated by reference, in its entirety, into the present application.

BACKGROUND OF THE INVENTION

1. Field of the Invention

The present invention relates to a solid phase carrier for carrying a bioactive substance, and a kit for measuring a measurement target substance in a biosample.

2. Description of the Related Art

The fluorescence detection method is widely used as a highly sensitive and easy measurement method for quantifying proteins, enzymes, inorganic compounds, and the like. The fluorescence detection method is a method of confirming the presence of a measurement target substance by detecting fluorescence emitted in a case where a sample considered to contain the measurement target substance emitting fluorescence by being excited by light having a specific wavelength is irradiated with excitation light having the specific wavelength. In a case where the measurement target substance is not a fluorescent substance, it is possible to confirm the presence of the measurement target substance, for example, by labeling a substance that binds specifically to the measurement target substance with a fluorescent dye, brining the labeled substance into contact with a sample, and then detecting the fluorescence emitted in a case where the sample is irradiated with excitation light in the same manner as described above.

As the fluorescence detection method described above, a method is known which exploits an electric field enhancing effect brought about by plasmon resonance so as to improve the detection sensitivity for a trace of measurement target substance present in a sample. In this method, in order to cause plasmon resonance, a sensor chip having a metal film provided in a predetermined area on a transparent support is prepared, and excitation light is caused to incident on the interface between the support and the metal film from one surface of the support opposite to the other surface thereof provided with the metal film at a predetermined angle equal to or larger than the angle of total reflection. Due to the irradiation with the excitation light, surface plasmon occurs on the metal film, and the occurrence of the surface plasmon enhances the electric field. As a result, fluorescence is enhanced, the signal/noise ratio (S/N ratio) is improved, and the measurement target substance can be measured with high sensitivity. The degree of signal enhancement obtained in the fluorescence detection method by surface plasmon excitation (hereinafter, called "SPF method") is about 10 times higher than the degree of signal enhancement obtained in the fluorescence detection method by epi-illumination excitation (also called epi-fluorescence illumination method). Therefore, with SPF method, a measurement target substance can be measured with high sensitivity.

WO2016/039293A describes, as a solid phase carrier inhibiting non-specific adsorption, a solid phase carrier to which a polymer having two kinds of structural units represented by predetermined formulas is bonded. WO2016/039293A also describes a ligand-bound solid phase carrier, a method for detecting or separating a target substance, and a method for manufacturing the solid phase carrier. In addition, JP2012-501963A describes an imaging agent for cells and/or tissues that feature fibrosis, which contains a polymer including retinoid and a detectable label bonded to each other.

SUMMARY OF THE INVENTION

Although the solid phase carrier described in WO2016/039293A has a high non-specific adsorption inhibitory effect, the ligand binding amount in this carrier is small. An object of the present invention is to provide a solid phase carrier for carrying bioactive substances, which achieves both the high non-specific adsorption inhibitory effect and high ligand binding amount. Another object of the present invention is to provide a kit for measuring a measurement target substance in a biosample, which includes the solid phase carrier.

In order to achieve the above objects, the inventors of the present invention conducted thorough studies. As a result, the inventors have found that in a case where a copolymer having a structural unit in which a hydrophilic group and a bioactive substance-reactive group are bonded to an acidic amino acid-derived group through a present linking group is caused to present on the surface of a solid phase, the above objects can be achieved. Based on the finding, the inventors have accomplished the present invention.

That is, according to an aspect of the present invention, the following inventions are provided.

[1] A solid phase carrier for carrying a bioactive substance, containing a copolymer having a structural unit represented by Formula (1), in which the copolymer is present on a surface of the solid phase.

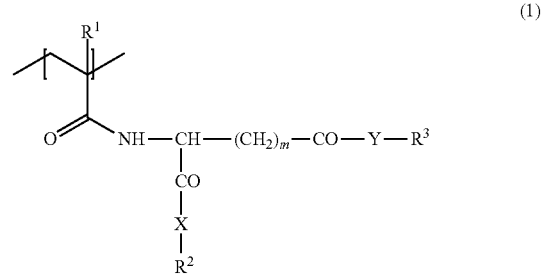

(1)

In the formula, $R^1$ represents a hydrogen atom or a methyl group;
X represents —NH— or —O—;
Y represents —NH— or —O—; and
m represents an integer from 1 to 5.
$R^2$ represents one of a hydrophilic group and a group represented by Formula (R-1), and $R^3$ represents the other.

(R-1)

n represents an integer of 1 to 12, $R^4$ represents a bioactive substance-reactive group, and * represents a position bonded to X or Y.

[2] The solid phase carrier described in [1], in which X is —NH—, and Y is —NH—.

[3] The solid phase carrier described in [1] or [2], in which m is 1 or 2.

[4] The solid phase carrier described in any one of [1] to [3], in which the hydrophilic group has a betaine structure, a sugar structure, an amino acid structure, or a sulfonic acid group.

[5] The solid phase carrier described in any one of [1] to [4], in which the bioactive substance-reactive group has a carboxyl group, an active ester, an isothiocyanate, an epoxy group, or a maleimide.

[6] The solid phase carrier described in any one of [1] to [5], in which n in Formula (R-1) is an integer of 3 to 6.

[7] The solid phase carrier described in any one of [1] to [6], in which a content of the bioactive substance-reactive group is 1 to 500 μmol per 1 g of a solid content of the solid phase carrier.

[8] The solid phase carrier described in any one of [1] to [7], in which the solid phase carrier is in the form of a particle.

[9] The solid phase carrier described in [8], in which the particle has a particle size of 50 to 300 nm.

[10] The solid phase carrier described in [8] or [9], in which a polydispersity index of the particle size of the particle is equal to or higher than 0.002 and equal to or lower than 0.10.

[11] The solid phase carrier described in any one of [8] to [10], in which the particle contains a fluorescent dye.

[12] The solid phase carrier described in [11], in which the fluorescent dye is an azadipyrromethene dye or a dipyrromethene dye.

[13] The solid phase carrier described in any one of [1] to [12], in which a bioactive substance is bonded to the bioactive substance-reactive group represented by $R^4$.

[14] The solid phase carrier described in [13], in which the bioactive substance is an antibody.

[15] A kit for measuring a measurement target substance in a biosample, including the solid phase carrier described in any one of [1] to [14]; and a substrate having a detection area on a metal film.

According to the solid phase carrier of an embodiment of the present invention, a high non-specific adsorption inhibitory effect and a high ligand binding amount can be achieved simultaneously. In a case where the kit according to an embodiment of the present invention is used for measurement, a high signal/noise ratio can be achieved.

DESCRIPTION OF THE PREFERRED EMBODIMENTS

Figure 1:
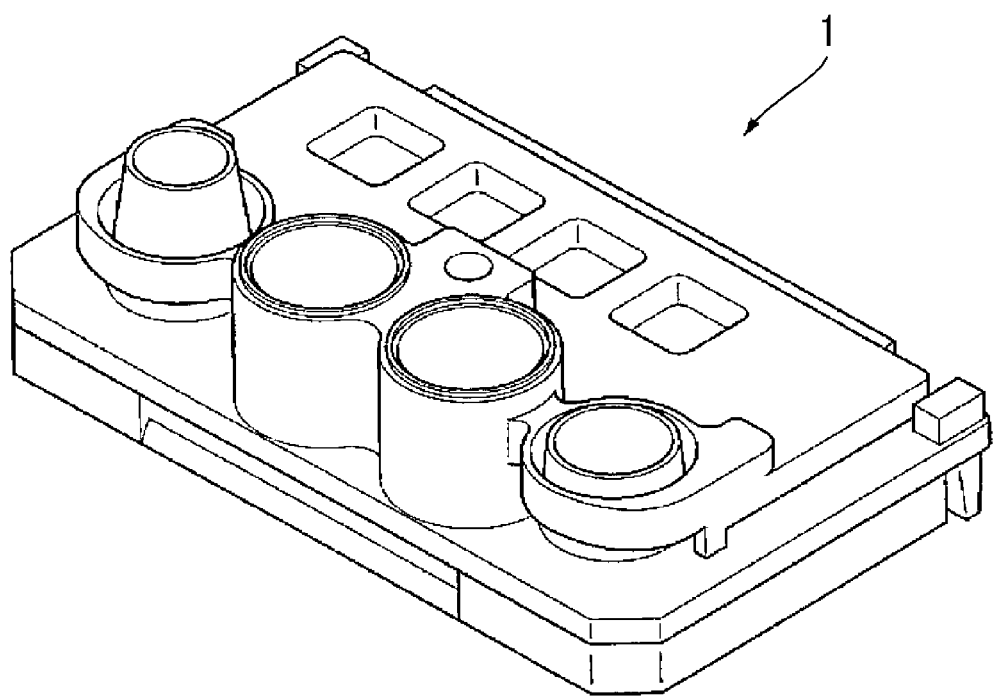
FIG. 1 is a schematic view of a sensor chip 1.

Hereinafter, embodiments of the present invention will be specifically described.

In the present specification, a range of numerical values described using "to" means a range including the numerical values listed before and after "to" as the minimum value and the maximum value respectively.

The solid phase carrier according to an embodiment of the present invention is a solid phase carrier for carrying a bioactive substance, which contains a copolymer having a structural unit represented by Formula (1). The copolymer is present on the surface of the solid phase. According to the solid phase carrier of the embodiment of the present invention, a high non-specific adsorption inhibitory effect and a high ligand binding amount can be achieved simultaneously. According to the kit which uses the solid phase carrier of the embodiment of the present invention and is for measuring a measurement target substance in a biosample, a test substance can be analyzed with high sensitivity.

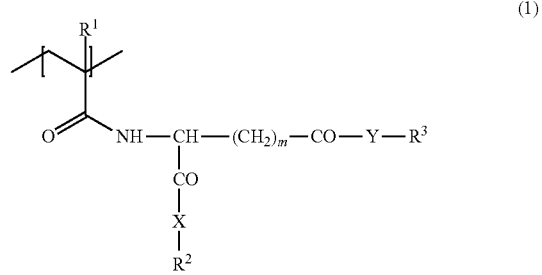

(1)

In the formula, $R^1$ represents a hydrogen atom or a methyl group;
X represents —NH— or —O—;
Y represents —NH— or —O—; and
m represents an integer from 1 to 5.
$R^2$ represents one of a hydrophilic group and a group represented by Formula (R-1), and $R^3$ represents the other.

(R-1)

n represents an integer of 1 to 12, $R^4$ represents a bioactive substance-reactive group, and * represents a position bonded to X or Y.
$R^1$ preferably represents a methyl group.
X is preferably —NH—, and Y is preferably —NH—. It is more preferable that X and Y both represent —NH—.
m is preferably 1 or 2.
It is preferable that the hydrophilic group represented by $R^2$ or $R^3$ has a betaine structure, a sugar structure, an amino acid structure, or a sulfonic acid group.

The betaine structure refers to a structure in which a portion carrying a positive charge and a portion carrying a negative charge are at nonadjacent positions in the same group, and a dissociable hydrogen atom is not bonded to an atom carrying a positive charge, which makes the structure chargeless and neutral overall. The portion carrying a positive charge is, for example, a portion having a cation structure such as quaternary ammonium, sulfonium, or phosphonium. Examples of the portion carrying a negative charge include a sulfonic acid group (—$SO_3^-$), a carboxylic acid group (—$COO^-$), a group derived from phosphoric acid (—$PO_4^-$—), and the like.

The sugar structure means a structure having a sugar group. Examples of the sugar include monosaccharides such as glucose, galactose, fructose, and mannose, disaccharides such as sucrose, lactose, maltose, trehalose, and fructose, and the like. However, the sugar is not particularly limited.

Examples of the amino acid structure include groups derived from natural amino acids (glycine, alanine, valine, leucine, isoleucine, serine, threonine, cysteine, methionine, asparagine, glutamine, proline, phenylalanine, tyrosine, tryptophan, aspartic acid, glutamic acid, lysine, arginine, and histidine). Furthermore, groups derived from other unnatural amino acids may also be used.

In the group represented by Formula (R-1) represented by $R^2$ or $R^3$, n represents an integer of 1 to 12. n is preferably an integer of 2 to 10, and more preferably an integer of 3 to 6.

$R^4$ represents a bioactive substance-reactive group. The bioactive substance-reactive group is preferably a group having a carboxyl group, an active ester, an isothiocyanate, an epoxy group, or a maleimide.

The content of the bioactive substance-reactive group represented by $R^4$ per 1 g of a solid content of the solid phase carrier is preferably 1 to 500 μmol, more preferably 10 to 500 μmol, even more preferably 100 to 500 μmol, particularly preferably 100 to 300 μmol, and most preferably 150 to 250 μmol.

Specific examples of the structural unit represented by Formula (1) will be shown below, but the present invention is not limited thereto.

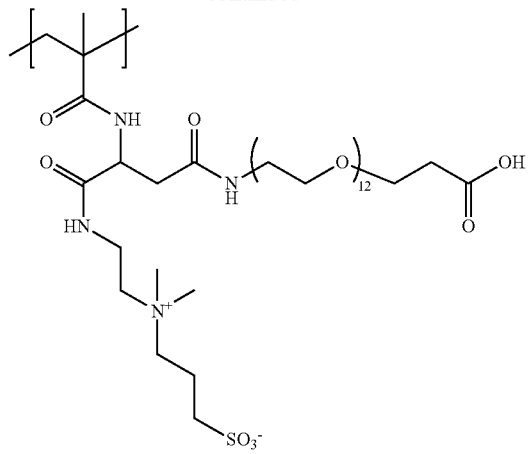

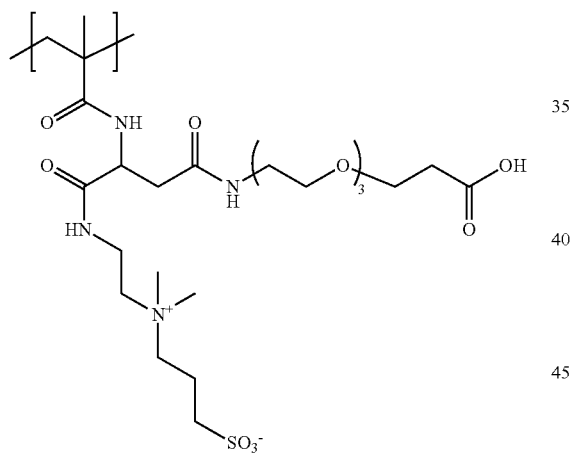

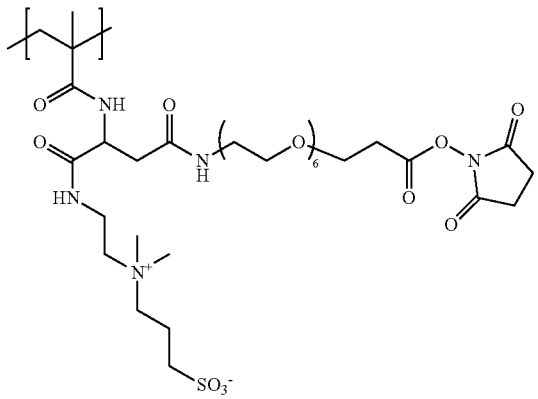

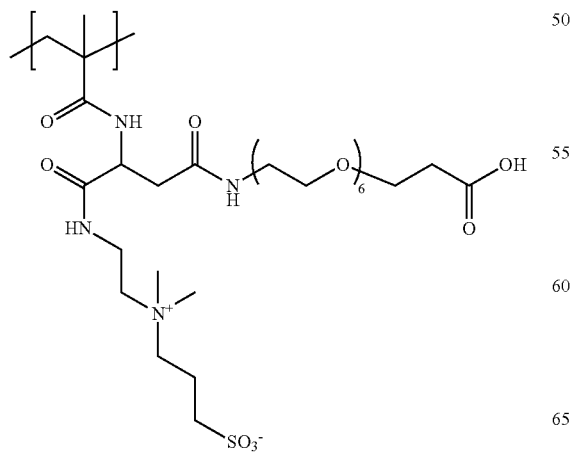

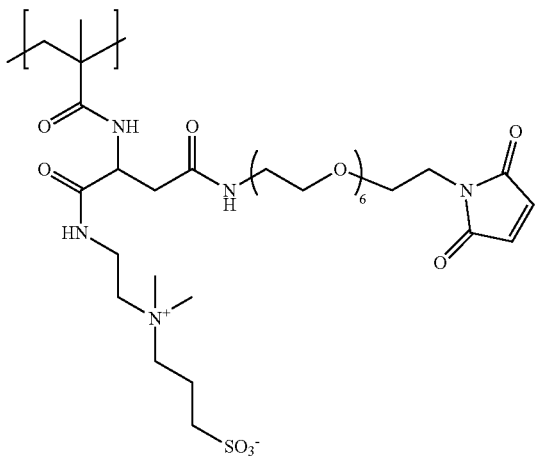

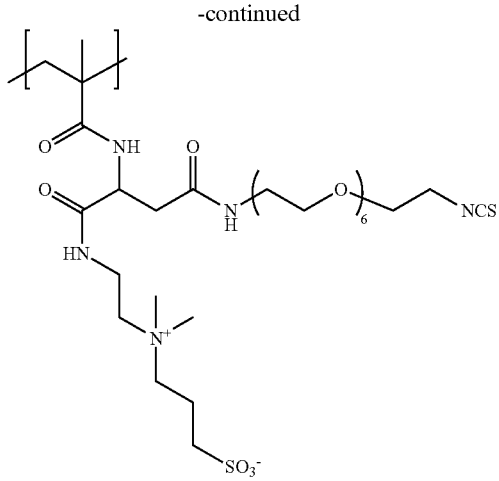
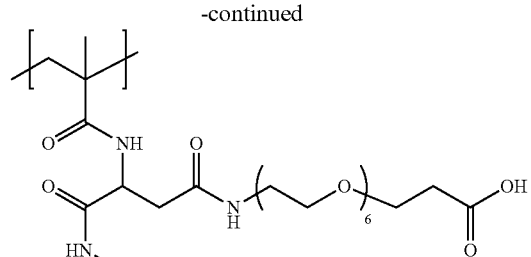
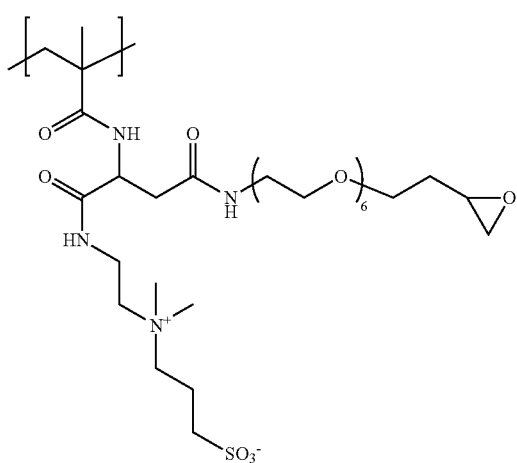
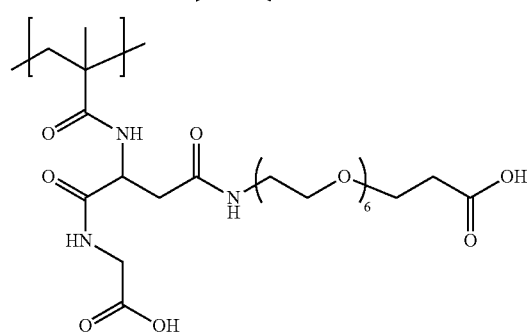
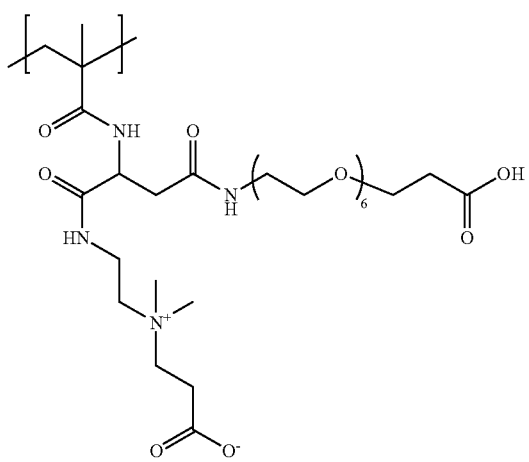
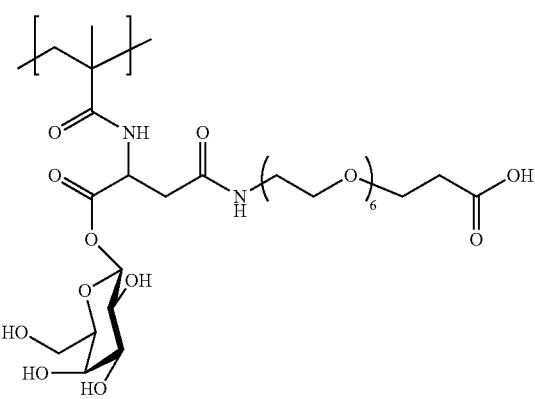

-continued

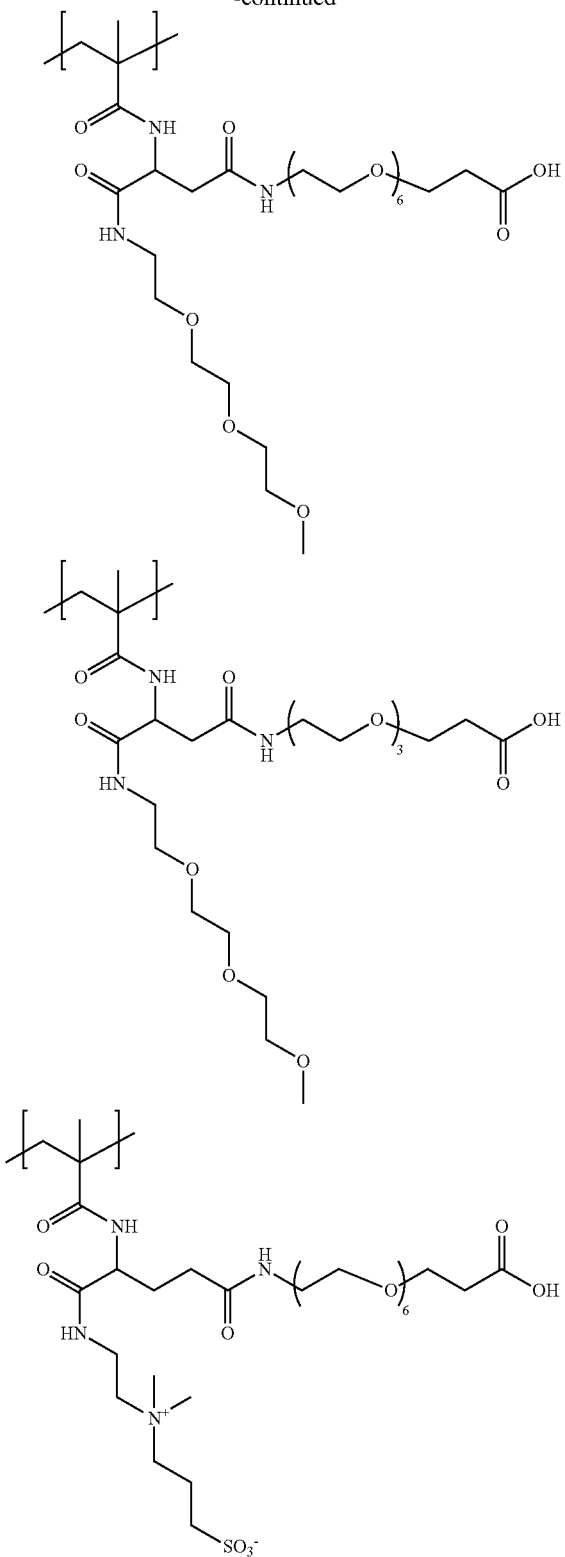

In the present invention, the solid phase carrier is preferably in the form of a particle. In this case, the solid phase carrier has an aspect in which it is a solid phase carrier for carrying a bioactive substance, wherein the copolymer having the structural unit represented by Formula (1) is present on the surface of the particle to be a core. As the particle to be a core, for example, a polymer particle such as a polystyrene bead and a glass particle such as a glass bead can be used. Specific examples of the material of the particle to be a core include polymers using monomers such as styrene, methacrylic acid, glycidyl (meth)acrylate, butadiene, vinyl chloride, vinyl acetate acrylate, methyl methacrylate, ethyl methacrylate, phenyl methacrylate, and butyl methacrylate and synthetic polymers such as copolymers using two or more monomers. Latex in which these are uniformly suspended is preferably used. Examples of the material of the particle to be a core also include other organic polymer powder, inorganic substance powder, microorganisms, blood cells, cell membrane fragments, liposomes, and the like.

In a case where a latex particle is used as the particle to be a core, specific examples of the material of the latex include polystyrene, a styrene-acrylic acid copolymer, a styrene-methacrylic acid copolymer, a styrene-glycidyl (meth)acrylate copolymer, a styrene-styrene sulfonate copolymer, a methacrylic acid polymer, an acrylic acid polymer, an acrylonitrile-butadiene-styrene copolymer, a vinyl chloride-acrylic acid ester copolymer, polyvinyl acetate acrylate, and the like. The latex is preferably a copolymer containing at least styrene as a monomer and particularly preferably a copolymer of styrene and an acrylic or methacrylic acid. The method for preparing the latex is not particularly limited. The latex can be prepared by any polymerization method. However, in a case where antibody labeling is performed in the presence of a surfactant, it is difficult to immobilize the antibody. Therefore, it is preferable that the latex is prepared by emulsifier-free emulsion polymerization, that is, emulsion polymerization in which an emulsifier such as a surfactant is not used.

The solid phase carrier according to the embodiment of the present invention contains a copolymer having a structural unit represented by Formula (1). The copolymer is present on the surface of the solid phase. The method for manufacturing the solid phase carrier according to the embodiment of the present invention is not particularly limited. For example, by preparing a particle to be a core of the solid phase carrier by the method described above, then adding a monomer compound corresponding to the structural unit represented by Formula (1) and, as desired, another monomer compound to the prepared particle to be a core, and polymerizing the monomer compounds, it is possible to manufacture a particle-like solid phase carrier in which the copolymer having the structural unit represented by Formula (1) is present on the surface of the particle to be a core.

It is preferable that the solid phase carrier (preferably a particle-like carrier, hereinafter, described as particle) according to the embodiment of the present invention contains a fluorescent dye. The fluorescent dye-containing particle can be prepared by adding a fluorescent dye to the particle to be a core. That is, the fluorescent dye-containing particle can be manufactured by adding a fluorescent dye to a solution of particles containing water and a water-soluble organic solvent and impregnating the particles with the fluorescent dye by means of stirring or the like.

Although the type of the fluorescent dye is not particularly limited, an azadipyrromethene dye or a dipyrromethene dye can be preferably used.

As the azadipyrromethene dye or the dipyrromethene dye, a compound represented by Formula (2) is preferable.

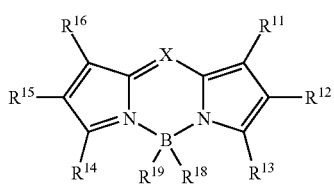 (2)

In the formula, X represents $CR^{17}$ or N.

$R^{11}$ to $R^{17}$ each represent a hydrogen atom, an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, a halogen atom, a cyano group, a formyl group, a R—CO— group, a carboxy group, a R—O—CO— group, a R—CO—O— group, a $(R^4)_2$N—CO— group, an amino group, a nitro group, or a silyl group. R represents an alkyl group, a cycloalkyl group, an aliphatic heterocyclic group, an alkenyl group, a cycloalkenyl group, an alkynyl group, an aryl group, or a heteroaryl group. $R^4$ represents a hydrogen atom, an alkyl group, a cycloalkyl group, an aliphatic heterocyclic group, an alkenyl group, a cycloalkenyl group, an alkynyl group, an aryl group, or a heteroaryl group.

$R^{18}$ and $R^{19}$ each represent an alkyl group, a cycloalkyl group, an aliphatic heterocyclic group, an alkenyl group, a cycloalkenyl group, an alkynyl group, a hydroxyl group, a mercapto group, an alkoxy group, an alkylthio group, an aryloxy group, an arylthio group, an aryl group, a heteroaryl group, or a halogen atom.

The alkyl group may be linear or branched. The number of carbon atoms in the linear or branched alkyl group is preferably 1 to 36, more preferably 1 to 18, even more preferably 1 to 12, and particularly preferably 1 to 6. Examples of the cycloalkyl group include cycloalkyl having 3 to 8 carbon atoms, and the like. Specific examples of the alkyl group and cycloalkyl group include a methyl group, an ethyl group, a n-propyl group, an isopropyl group, a n-butyl group, an iso-butyl group, a sec-butyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a cyclohexyl group, and the like.

The aliphatic heterocyclic group is not particularly limited, and examples thereof include groups derived from a 2-oxopyrrolidine ring, a piperidine ring, a piperazine ring, a morpholine ring, a tetrahydrofuran ring, a tetrahydropyran ring, a tetrahydrothiophene ring, and the like.

The alkenyl group may be linear or branched. The number of carbon atoms in the linear or branched alkenyl group is preferably 2 to 36, more preferably 2 to 18, even more preferably 2 to 12, and particularly preferably 2 to 6. Examples of the alkenyl group include a vinyl group, an allyl group, a prenyl group, a geranyl group, an oleyl group, and the like. Examples of the cycloalkenyl group include a cycloalkenyl group having 3 to 8 carbon atoms. Examples of the cycloalkenyl group include a 2-cyclopenten-1-yl group, a 2-cyclohexen-1-yl group, and the like.

The alkynyl group may be linear or branched. The number of carbon atoms in the linear or branched alkynyl group is preferably 2 to 36, more preferably 2 to 18, even more preferably 2 to 12, and particularly preferably 2 to 6. Examples of the alkynyl group include an ethynyl group, a propargyl group, and the like.

The alkoxy group is preferably an alkoxy group having 1 to 20 carbon atoms. Examples thereof include a methoxy group, an ethoxy group, a propoxy group, an n-butoxy group, a pentyloxy group, a hexyloxy group, a heptyloxy group, and the like.

The alkylthio group is preferably an alkylthio group having 1 to 30 carbon atoms. Examples thereof include a methylthio group, an ethylthio group, a n-hexadecylthio group, and the like.

The aryloxy group is preferably an aryloxy group having 6 to 14 carbon atoms. Examples thereof include a phenoxy group, a naphthoxy group, an anthryloxy group, and the like.

The arylthio group is preferably an arylthio group having 6 to 30 carbon atoms. Examples thereof include a phenylthio group, a p-chlorophenylthio group, a m-methoxyphenylthio group, and the like.

The aryl group is preferably an aryl group having 6 to 48 carbon atoms, more preferably an aryl group having 6 to 24 carbon atoms, and even more preferably an aryl group having 6 to 14 carbon atoms. Examples thereof include a phenyl group, a naphthyl group, an anthryl group, a pyrenyl group, a phenanthrenyl group, a biphenyl group, a fluorenyl group, and the like.

The heteroaryl group is preferably any of 5- to 7-membered substituted or unsubstituted, saturated or unsaturated, and monocyclic or condensed heterocyclic groups. The heteroaryl group is preferably a heteroaryl group having a ring-constituting atom selected from a carbon atom, a nitrogen atom, an oxygen atom, and a sulfur atom and having at least one heteroatom which is a nitrogen atom, an oxygen atom, or a sulfur atom. The heteroaryl group is more preferably a 5- or 6-membered heteroaryl group having 3 to 30 carbon atoms. Examples of the heteroaryl group include an imidazolyl group, a pyridyl group, a quinolyl group, a furyl group, a thienyl group, a benzoxazolyl group, an indolyl group, a benzimidazolyl group, a benzthiazolyl group, a carbazolyl group, an azepinyl group, and the like.

Examples of the halogen atom include a fluorine atom, a chlorine atom, a bromine atom, and an iodine atom.

Examples of the amino group include an amino group; an alkyl-substituted amino group such as a mono- or dimethylamino group, a mono or di-ethylamino group, and a mono- or di(n-propyl)amino group; an amino group substituted with an aromatic residue such as a mono- or diphenylamino group and a mono- or dinaphthylamino group; an amino group substituted with one alkyl group and one aromatic residue such as a monoalkyl monophenylamino group; a benzylamino group, an acetylamino group, a phenylacetylamino group, and the like. The aromatic residue means a group obtained by removing one hydrogen atom from an aromatic ring.

The aforementioned groups represented by $R^{11}$ to $R^{19}$ may have a substituent. Examples of the substituent include substituents described in the following substituent group A. The substituents in the substituent group A may be further substituted with the substituents in the substituent group A. Substituent Group A:

a sulfamoyl group, a cyano group, an isocyano group, a thiocyanato group, an isothiocyanato group, a nitro group, a nitrosyl group, a halogen atom, a hydroxy group, an amino group, a mercapto group, an amide group, an alkoxy group, an aryloxy group, an alkylthio group, an arylthio group, a carbamoyl group, an acyl group, an aldehyde group, a carbonyl group, an aryl group, an alkyl group, an alkyl group substituted with a halogen atom, an ethenyl group, an ethynyl group, a silyl group, and a trialkylsilyl group (such as a trimethylsilyl group).

The particle size of the particle in the present invention is preferably within a range of 50 nm to 300 nm, more preferably within a range of 60 nm to 250 nm, and even more preferably within a range of 70 nm to 200 nm.

The particle size may refer to the particle size of a particle containing a fluorescent dye (hereinafter, also called fluorescent particle) in a case where the particle contains a fluorescent dye or may refer to the particle size of a particle that does not contain a fluorescent dye.

The average particle size of the particle and the fluorescent particle can be measured using a commercial particle size distribution analyzer or the like. As particle size distribution measurement methods, optical microscopy, confocal laser microscopy, electron microscopy, atomic force microscopy, a static light scattering method, laser diffractometry, a dynamic light scattering method, centrifugal sedimentation, electric pulse sensing, chromatography, an ultrasonic attenuation method, and the like are known. Devices employing the respective principles of these methods are commercially available.

From the viewpoint of particle size range and ease of measurement, in the present invention, it is preferable to use the dynamic light scattering method. Examples of commercial measurement devices exploiting dynamic light scattering include NANOTRAC UPA (NIKKISO CO., LTD.), a dynamic light scattering particle size distribution analyzer LB-550 (HORIBA, Ltd.), a concentrated-system particle size analyzer FPAR-1000 (OTSUKA ELECTRONICS Co., Ltd), ZETA SIZER Nano series (Malvern Panalytical), and the like. In the present invention, a median diameter (d=50) measured at a temperature of 25° C. is adopted as the average particle size.

The polydispersity index (PDI) of the particle and the fluorescent particle is an index for evaluating the width of particle size distribution. The values of PDI ranges from 0 to 1. The polydispersity index value of 0 represents an ideal particle size distribution with no size distribution. A dispersion having a PDI value equal to or lower than 0.1 is regarded as being monodispersed. A dispersion having a PDI value of 0.1 to 0.3 is regarded as having a narrow size distribution. A dispersion having a PDI value higher than 0.5 is polydispersed. The polydispersity index is calculated from the values obtained using a dynamic light scattering (DLS) method. In the present invention, the polydispersity index is preferably equal to or higher than 0.0001 and equal to or lower than 0.2, more preferably equal to or higher than 0.001 and equal to or lower than 0.15, and even more preferably equal to or higher than 0.002 and equal to or lower than 0.10.

<Bioactive Substance>

In the present invention, a bioactive substance can be bonded to the bioactive substance-reactive group represented by $R^4$ in Formula (1).

As the bioactive substance to be bonded to the bioactive substance-reactive group reactive by $R^4$, a binding substance (hereinafter, also called first binding substance) binding to a measurement target substance is preferable. An antigen, an antibody, or a complex of these can be used as the first binding substance, but the first binding substance is not limited to these. The bioactive substance (that is, the first binding substance) is preferably an antibody.

The antibody can be used regardless of the animal species, subclass, and the like. For example, in the present invention, it is possible to use antibodies derived from immunoreactive organisms such as mice, rats, hamsters, goats, rabbits, sheep, cows, and chickens. Specifically, the antibodies include mouse IgG, mouse IgM, rat IgG, rat IgM, hamster IgG, hamster IgM, rabbit IgG, rabbit IgM, goat IgG, goat IgM, sheep IgG, sheep IgM, bovine IgG, bovine IgM, chicken IgY, and the like. Furthermore, both the monoclonal and polyclonal antibodies can be used.

The antibody may be a commercial antibody. Alternatively, it is possible to use an antibody prepared from animal serum or culture supernatant by a known method. For example, it is possible to use an antiserum prepared from the serum of an animal immunized with a measurement target substance, an immunoglobulin fraction purified from an antiserum, or antibodies obtained by cell fusion using spleen cells of an animal immunized with a measurement target substance.

As the antibody, an antibody fragment may also be used. The antibody fragment is a molecule which has at least one antigen binding site and is derived from a full-size antibody. Specifically, there are antibody fragments such as $F(ab')_2$, Fab, Fab', and Fv. These antibody fragments are molecules obtained by enzymatic or chemical treatments or by genetic engineering techniques. The antibody may be a modified antibody such as a chimeric antibody.

By causing a reaction between the bioactive substance-reactive group represented by $R^4$ and a bioactive substance (the first binding substance, for example, an antibody), it is possible to bond the bioactive substance to the copolymer having the structural unit represented by Formula (1). For example, it is possible to use a method of causing a dehydration reaction between a carboxyl group converted into an active ester in the copolymer having the structural unit represented by Formula (1) and an amino group of a bioactive substance (the first binding substance, for example, an antibody) by using a water-soluble carbodiimide so that the copolymer and the bioactive substance are bonded to each other.

<Kit>

The present invention relates to a kit for measuring a measurement target substance in a biosample, which includes the solid phase carrier according to the embodiment of the present invention described above and a substrate comprising a detection area on a metal film (that is, a substrate including a metal film and a detection area on the metal film).

The measurement target substance may be a substance present in the biosample. The biosample is not particularly limited as long as it is a sample that is likely to contain the measurement target substance. Examples of thereof include biological samples, particularly, body fluid (for example, blood, serum, plasma, spinal fluid, tears, sweat, urine, pus, nasal discharge, or sputum), excrement (for example, feces), organs, tissues, mucous membranes, and skin of animals (for example, a human being, a dog, and a cat), and the like.

The measurement target substance is not particularly limited, and examples thereof include cholesterol, hormones (such as steroid hormones and peptide hormones), proteins, bile acid, cortisol, and the like. As the measurement target substance, for example, thyroid stimulating hormone (TSH) or progesterone is particularly preferable.

(Substrate)

In the present invention, in order to measure a measure target sample with high sensitivity, it is preferable to adopt a measurement method in which surface plasmon-enhanced fluorescence (SPF), which will be described later, is detected. In this case, as a substrate, it is preferable to use a substrate having a metal film on a surface thereof. The metal constituting the metal film is not particularly limited as long as surface plasmon resonance can occur. As the metal, for example, free electron metals such as gold, silver, copper, aluminum, and platinum are preferable. Among these, gold is particularly preferable. In a case where gold is used, the detection area which will be describe later is on the gold film. The metals described above can be used singly or used in combination. Furthermore, considering the adhesiveness of the metal to the substrate, an interlayer formed of chromium or the like may be provided between the substrate and a layer formed of the metal. The film thickness of the metal film is arbitrarily set. For example, the metal film thickness is preferably equal to or greater than 1 nm and equal to or smaller than 500 nm, and particularly preferably equal to or greater than 10 nm and equal to or smaller than 200 nm. In a case where the metal film thickness is greater than 500 nm, the surface plasmon phenomenon of a medium cannot be sufficiently detected. Furthermore, in a case where an interlayer formed of chromium or the like is provided, the thickness of the interlayer is preferably equal to or greater than 0.1 nm and equal to or smaller than 10 nm.

The metal film may be formed by a conventional method. For example, the metal film can be formed by a sputtering method including a magnetron sputtering method, a vapor deposition method, an ion plating method, an electroplating method, an electroless plating method, or the like. In order to improve the adhesiveness of the metal film by providing a mixed layer of the substrate material and the metal film, it is preferable to prepare the metal film by a sputtering method. In this case, the thickness of the mixed layer of the substrate material and the metal film is not particularly limited as long as sufficient adhesiveness can be ensured. The thickness of the mixed layer is preferably equal to or smaller than 10 nm.

It is preferable that the metal film is disposed on the substrate. Herein, "disposed on the substrate" means that the metal film is disposed to come into direct contact with the substrate or means that the metal film is disposed on the substrate through another layer and does not come into direct contact with the substrate. In the present invention, as the substrate, for example, it is possible to use substrates formed of materials transparent to laser light such as optical glass like BK7 (borosilicate glass) which is a sort of general optical glass or synthetic resins, specifically, polymethylmethacrylate, polyethylene terephthalate, polycarbonate, and a cycloolefin polymer. The substrate is preferably a material that does not exhibit anisotropy with respect to polarized light and has excellent workability.

As a preferred aspect of the substrate for SPF detection, for example, a substrate can be exemplified which is obtained by vapor-depositing a gold film on polymethylmethacrylate (PMMA).

The substrate comprises a detection area having a second binding substance binding to any of a measurement target substance or a bioactive substance (the first binding substance) on the metal film.

(Second Binding Substance)

The second binding substance is a substance binding to a measurement target substance or to a bioactive substance (the first binding substance). In a case where quantification is performed by a sandwich assay method, a substance binding to the measurement target substance can be used as the second binding substance. In a case where quantification is performed by a competitive method, a substance binding to a bioactive substance (the first binding substance) can be used as the second binding substance.

The second binding substance is not particularly limited. As the second binding substance, for example, an antigen, an antibody, and a complex of these are preferable. In a case where an antigen is used as the second binding substance, it is preferable to use a measurement target substance (substance binding to the first binding substance) or a hapten thereof. In a case where a measurement target substance or a hapten thereof is used as the second binding substance, a conjugate of the measurement target substance and a carrier is preferable as the second binding substance. The carrier means a substance to which a plurality of molecules of the measurement target substance can bind. As the carrier, for example, a protein and the like are preferable. Specifically, examples thereof include bovine serum albumin and the like.

In a case where an antibody is used as the second binding substance, as the method of immobilizing the antibody onto the metal film on the substrate, it is possible to adopt any of the principles of physical adsorption or chemical bonding by covalent bonds. Furthermore, in order to prevent metal-induced quenching, it is possible to use a method of forming a self-assembled monolayer (SAM) on the metal film and immobilizing the second binding substance onto the SAM membrane or a method of additionally providing a hydrophilic polymer layer such as carboxymethyl dextran (CMD) on SAM and immobilizing the second binding substance onto the hydrophilic polymer layer.

Typically, in a case where an alcanethiol compound is brought into contact with and left on the surface of a metal film containing gold, the alcanethiol compound reacts with the surface containing gold, a Au—S bond is formed, and alkyl chains interact with each other. As a result, the self-assembled monolayer (SAM), which is known as a highly oriented monolayer, is formed on the gold surface. Therefore, SAM is widely used in the field of surface plasmon resonance/fluorescence, quartz crystal microbalance (QCM), or the like.

Specific examples of SAM include a membrane formed of 1-undecanethiol, 10-carboxy-1-decanethiol, or 11-hydroxy-1-undecanethiol, a membrane in which these are combined, and the like.

It is preferable to provide a hydrophilic polymer layer on SAM described above. The hydrophilic polymer layer is provided so that a two-dimensional or three-dimensional structure is formed on SAM. Particularly, in a case where a three-dimensional structure is provided, it is possible to prepare a hydrophilic polymer layer structure in which the second binding substance is immobilized not only onto the two-dimensional space, the surface of the support, but also to a three-dimensional space separated from the surface of the metal film on the substrate.

Specific examples of the hydrophilic polymer include at least one kind of polymer selected from the group consisting of a polysaccharide, polyethylene glycol, a polyacrylic acid, and a polymethacrylic acid. The polysaccharide is preferably a hydrophilic polymer such as dextran or a dextran derivative. From the viewpoint of improving biocompatibility or further inhibiting a non-specific adsorption reaction, it is preferable that the hydrophilic polymer layer is constituted with dextran such as carboxymethyl dextran (CMD).

In a case where an antibody is used as the second binding substance, the antibody can be immobilized onto the hydrophilic polymer layer, for example, by a method in which a carboxyl group of a polymer having a reactive functional group such as carboxymethyldextran (CMD) is converted into an active ester by a water-soluble carbodiimide (WSC) such as 1-ethyl-3-(3-dimethylaminopropyl) carbodiimide hydrochloride (EDC) and N-hydroxysuccinimide (NHS), and a dehydration reaction is caused between the carboxyl group converted into the active ester and an amino group of the antibody as the second binding substance by using a water-soluble carbodiimide so that the antibody is immobilized.

<Detection Area (Test Area)>

In the present invention, a detection area (test area) for testing for the presence or absence of a measurement target substance is provided on the substrate. In this detection area, antigen quantification can be performed, for example, by capturing antigens as a measurement target substance and detecting and quantifying the amount of labels bound to the antigens. Alternatively, antigen quantification can be performed by a method in which only the labels bound to antigens are prevented from binding to the substrate, only the labels bound to the antigens are captured, and the amount of labels bound to the antigens is calculated.

<Other Elements of Kit>

The kit according to the embodiment of the present invention is used for a method of measuring a measurement target substance. In a case where thyroid stimulating hormone (TSH) is a measurement target substance, the kit is used as a measurement and diagnostic kit for TSH. The kit according to the embodiment of the present invention used for measuring a measurement target substance includes the solid phase carrier according to an embodiment of the present invention; and a substrate comprising a detection area having the second binding substance on a metal film. The kit may also include various tools or devices used for measuring a measurement target substance, such as a surface plasmon excitation device and a fluorometer. Furthermore, the kit may also include elements such as a sample containing a known quantity of measurement target substance and an instruction manual.

<Competitive Method>

As an example of the competitive method, progesterone quantification will be described below. Substances other than progesterone can also be quantified by the same method.

First, a progesterone immunoassay substrate onto which a progesterone•albumin conjugate is immobilized is brought into contact with a biosample being likely to contain progesterone and the solid phase carrier according to an embodiment of the present invention having a fluorescent dye and an anti-progesterone antibody. In a case where the biosample does not contain progesterone, by the anti-progesterone antibody on the solid phase carrier and the progesterone on the substrate (that is, the progesterone in the progesterone•albumin conjugate), an antigen-antibody reaction occurs on the substrate. On the other hand, in a case where the biosample contains progesterone, an antigen-antibody reaction occurs between the progesterone in the biosample and the anti-progesterone antibody on the solid phase carrier, and an antigen-antibody reaction between the anti-progesterone antibody on the solid phase carrier and the progesterone on the substrate (that is, the progesterone in the progesterone•albumin conjugate) is inhibited. After the above reaction ends, the anti-progesterone antibody on the solid phase carrier that did not bind to albumin on the substrate is removed. Then, the degree of formation of an immune complex on the substrate (that is, a complex of the anti-progesterone antibody on the solid phase carrier and the progesterone in the progesterone•albumin conjugate on the substrate) is detected as fluorescence intensity. Through the above process, it is possible to measure the concentration of progesterone in a biosample and the like.

In the competitive method, fluorescence can be measured by a plate reader or flow cytometry. For example, the fluorescence can be measured by the following method. A plurality of samples containing a known quantity of progesterone having different progesterone concentrations is prepared in advance, and these samples and the solid phase carrier according to an embodiment of the present invention are mixed in advance. The obtained mixed solution is brought into contact with the area where the progesterone•albumin conjugate is immobilized. While the mixed solution is in contact with the conjugate at specific time intervals, fluorescence signals from the area where the progesterone•albumin conjugate is immobilized are measured as a plurality of fluorescence signals. From the plurality of fluorescence signals, the temporal change (slope) of fluorescence amount at each progesterone concentration is determined. The temporal change is plotted on the Y-axis, the progesterone concentration is plotted on the X-axis, and a relational expression of the progesterone concentration to the temporal change of the fluorescence amount is obtained using an appropriate fitting method such as the least square method. Based on the relational expression obtained in this way, by utilizing the result of the temporal change of fluorescence amount using a biosample for test, the progesterone contained in the biosample can be quantified.

It is preferable that the progesterone quantification is finished in a short time. Specifically, the quantification is preferably finished in 10 minutes, more preferably finished in 8 minutes, and even more preferably finished in 6 minutes. The quantification time preferably includes the time for which a sample and a fluorescent-labeled anti-progesterone antibody are brought into contact with the detection area, where the progesteroneΨalbumin conjugate is immobilized, by using the relational expression between the temporal change of the fluorescence amount and the progesterone concentration obtained in advance by using an appropriate fitting method such as the least square method and then the amount of progesterone contained in a biosample is calculated based on the result of the temporal change of the fluorescence amount using the biosample for test.

<Sandwich Method>

As an example of the sandwich method, TSH quantification will be described below. Substances other than TSH can also be quantified by the same method.

First, a biosample being likely to contain TSH and the solid phase carrier according to an embodiment of the present invention having a fluorescent dye and an anti-TSH antibody 2 are brought into contact with a TSH immunoassay substrate onto which an anti-TSH monoclonal antibody 1 is immobilized. In a case where the biosample contains TSH, by TSH which has undergone an antigen-antibody reaction with the anti-TSH antibody 2 and the anti-TSH antibody 1 on the substrate, an antigen-antibody reaction occurs on the substrate. On the other hand, in a case where the biosample does not contain TSH, no antigen-antibody reaction occurs between the anti-TSH antibody 2 mixed with the biosample and the anti-TSH antibody 1 on the substrate. After the above reaction ends, the anti-TSH antibody 2 that did not bind to the anti-TSH antibody 1 on the substrate is removed. Then, the degree of formation of an immune complex on the substrate (that is, a complex of the fluorescent-labeled anti-TSH antibody 2, TSH, and the anti-TSH antibody 1 on the substrate) is detected as fluorescence intensity. Through this process, the concentration of a measurement target substance and the like can be measured. The fluorescence intensity and the concentration of a measurement target substance are positively correlated.

(Flow Channel)

In a preferred aspect of the present invention, a mixed solution obtained by mixing a biosample being likely to contain a measurement target substance with the solid phase carrier according to an embodiment of the present invention can be applied to the substrate and developed through a flow channel. The flow channel is not particularly limited as long as it functions as a passage that allows the biosample and the solid phase carrier according to the embodiment of the present invention to flow down to the detection area. In a preferred aspect, the flow channel includes a dispensing port for dispensing a biosample solution and a metal film as a detection area, keeps running from the metal film, and has a structure that enables the biosample to pass over the metal film. An aspiration port can be provided preferably on a side facing the dispensing port across the metal film.

(Surface Plasmon Fluorometry)

The method of detecting a label such as fluorescence in the present invention is not particularly limited. For example, it is preferable to detect fluorescence intensity by using an instrument that can detect fluorescence intensity, specifically, a microplate reader, a biosensor for detecting fluorescence by surface plasmon excitation (SPF), or the like. The label information relating to the amount of a measurement target substance can be obtained preferably through fluorescence detection by surface plasmon resonance.

The fluorescence may be measured by a plate reader or flow cytometry. The fluorescence detection method by surface plasmon excitation (SPF method) makes it possible to measure fluorescence with higher sensitivity, compared to a fluorescence detection method by epi-illumination excitation (epi-fluorescence illumination method).

As a surface plasmon fluorescence (SPF) biosensor, for example, it is possible to use the sensor described in JP2008-249361A, which comprises an optical waveguide formed of a material transmitting excitation light having a predetermined wavelength, a metal film formed on one surface of the optical waveguide, a light source generating a light beam, an optical system that causes the light beam to pass through the optical waveguide and to be incident on the interface between the optical waveguide and the metal film at an angle of incidence at which the surface plasmon occurs, and a fluorescence detection unit for detecting fluorescence excited and generated by the surface plasmon-enhanced evanescent waves.

The fluorescence detection (SPF) system by surface plasmon excitation is preferably an assay method for detecting fluorescence from a fluorescent substance depending on the amount of a measurement target substance immobilized on the metal film on the substrate. This method is different, for example, from a so-called latex agglutination method in which a change in optical transparency is detected as turbidity with the progress of the reaction in a solution. In the latex agglutination method, antibody-sensitized latex in a latex reagent and an antigen in a biosample are conjugated and agglutinated by an antibody response, and the agglutinate grows over time. The latex agglutination method is a method of quantifying antibody concentration from the change in absorbance per unit time obtained by irradiating the agglutinate with near infrared light. The present invention can provide a method for detecting a measurement target substance that is much simpler than the latex agglutination method.

Hereinafter, the present invention will be more specifically described based on examples of the present invention. The materials, amounts and proportions of the materials, details and procedures of treatments, and the like described in the following examples can be appropriately changed as long as the gist of the present invention is maintained. Therefore, the scope of the present invention is not limited to the following specific examples.

EXAMPLES

The abbreviations stand for the following.
Bn: benzyl
Boc: tert-butoxycarbonyl
t-Bu: tert-butyl
r. t.: room temperature Monomer Synthesis Synthesis Example 1

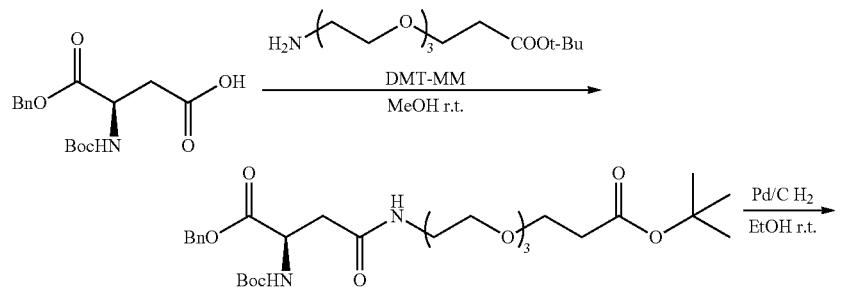

Compound 1-A

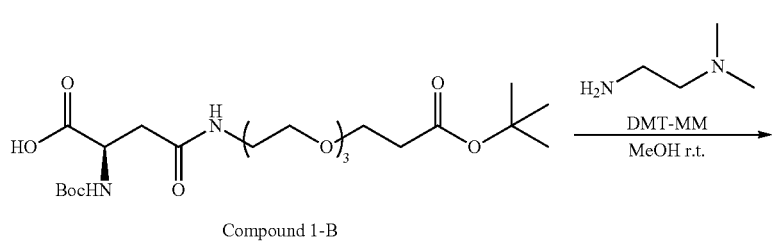

Compound 1-B

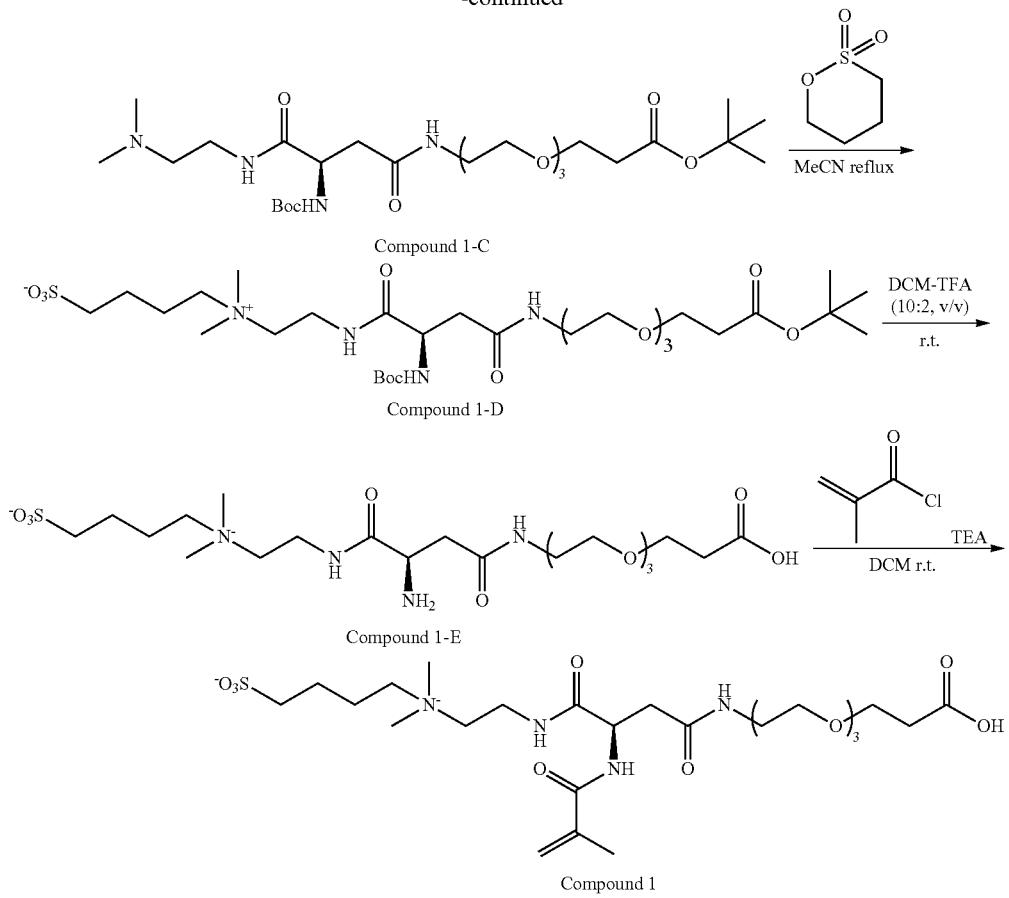

Compound 1-C

Compound 1-D

Compound 1-E

Compound 1

Synthesis of Compound 1-A

In a 100 mL three-neck eggplant flask, 700 mg of N-(tert-butoxycarbonyl)-L-aspartic acid 1-benzyl and 900 mg of amino-PEG3-tert-butyl ester were dissolved in methanol (MeOH). Under ice cooling, 1.057 g of 4-(4,6-dimethoxy-1,3,5-triazin-2-yl)-4-methylmorpholinium chloride (DMT-MM) was added to the solution and allowed to react at room temperature for 4 hours. After the reaction ended, the solvent was distilled off under reduced pressure. The residue was dissolved in 40 mL of ethyl acetate and washed with saturated aqueous sodium bicarbonate, saturated aqueous ammonium chloride, and saturated saline, and the organic layer was dried over sodium sulfate. The solvent was distilled off under reduced pressure, and the residue was purified by column chromatography (methylene chloride→methylene chloride/methanol=96/4), thereby obtaining 1.345 g of a compound 1-A at a yield of 98%.

Synthesis of Compound 1-B

Ethanol (EtOH, 30 mL) was added to 1.34 g of the compound 1-A and 370 mg of 10% Pd/C, and the mixture was allowed to react in an autoclave at 25° C. for 9 hours in a hydrogen atmosphere. After the reaction ended, Pd/C was filtered off through celite, and the solvent was distilled off under reduced pressure, thereby obtaining 1.11 g of a compound 1-B at a yield of 98%.

Synthesis of Compound 1-C

In a 50 mL eggplant flask, 574 mg of the compound 1-B and 186 μL of N,N-dimethylethylenediamine were dissolved in 9 mL of methanol (MeOH). Under ice cooling, 563 mg of 4-(4,6-dimethoxy-1,3,5-triazin-2-yl)-4-methylmorpholinium chloride (DMT-MM) was added to the solution and allowed to react at room temperature for 24 hours. After the reaction ended, the solvent was distilled off under reduced pressure. The residue was dissolved in methylene chloride and washed with saturated aqueous sodium bicarbonate, saturated aqueous ammonium chloride, and saturated saline, and the organic layer was dried over sodium sulfate. The solvent was distilled off under reduced pressure, and the residue was purified by column chromatography (methylene chloride/methanol=80/20), thereby obtaining 477 mg of a compound 1-C at a yield of 73%.

Synthesis of Compound 1-D

Acetonitrile (MeCN, 1 mL) was added to 477 mg of the compound 1-C and 230 μL of 1,4-butansultone, and the mixture was allowed to react in a microwave at 100° C. for 3 hours. The solvent was distilled off under reduced pressure, and the residue was purified by reverse-phase column chromatography (water/acetonitrile=90/10→water/acetonitrile=50/50), thereby obtaining 428 mg of a compound 1-D at a yield of 72%.

Synthesis of Compound 1-E

In a 50 mL eggplant flask, 428 mg of the compound 1-D was dissolved in 6 mL of methylene chloride (DCM). Trifluoroacetic acid (TFA, 1.2 mL) was added thereto and allowed to react for 24 hours. After the reaction ended, methylene chloride and trifluoroacetic acid were distilled off under reduced pressure, and the residue was purified by reverse-phase column chromatography (water→water/acetonitrile=90/10), thereby obtaining 78 mg of a compound 1-E at a yield of 20%.

Synthesis of Compound 1

In a 50 mL eggplant flask, 78 mg of the compound 1-E and 26 μL of triethylamine (TEA) were dissolved in 2 mL of methylene chloride (DCM). Methacryloyl chloride (17 μL) was added thereto and allowed to react for 16 hours. After the reaction ended, the solvents were distilled off under reduced pressure, and the residue was purified by reverse-phase column chromatography (water/acetonitrile=90/10→water/acetonitrile=70/30), thereby obtaining 50 mg of a compound 1 at a yield of 80%.

Synthesis Example 2

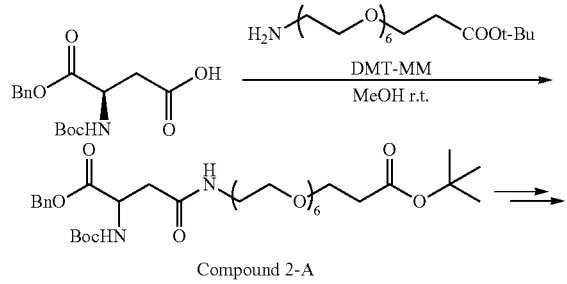

Compound 2-A

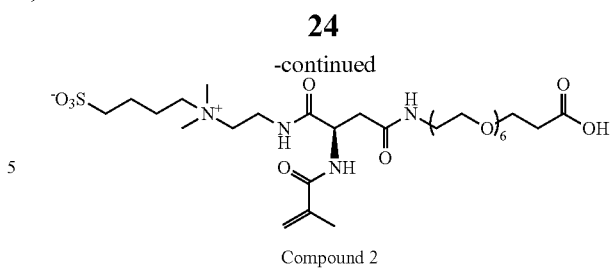

Compound 2

A compound 2 was synthesized in the same manner as in Synthesis Example 1, except that the used raw materials were changed.

Synthesis Example 3

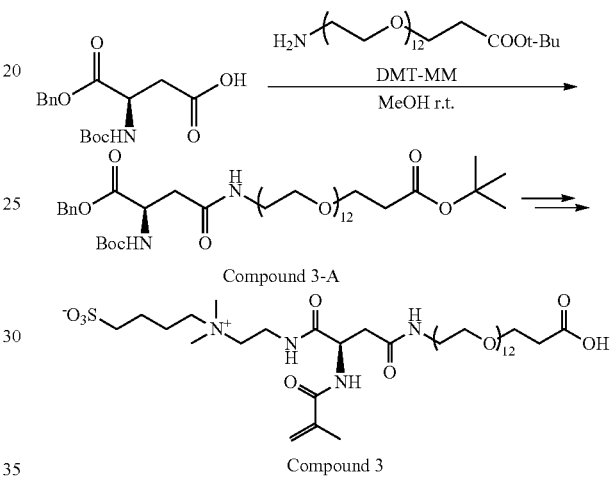

Compound 3-A

Compound 3

A compound 3 was synthesized in the same manner as in Synthesis Examples 1 and 2, except that the used raw materials were changed.

Synthesis Example 4

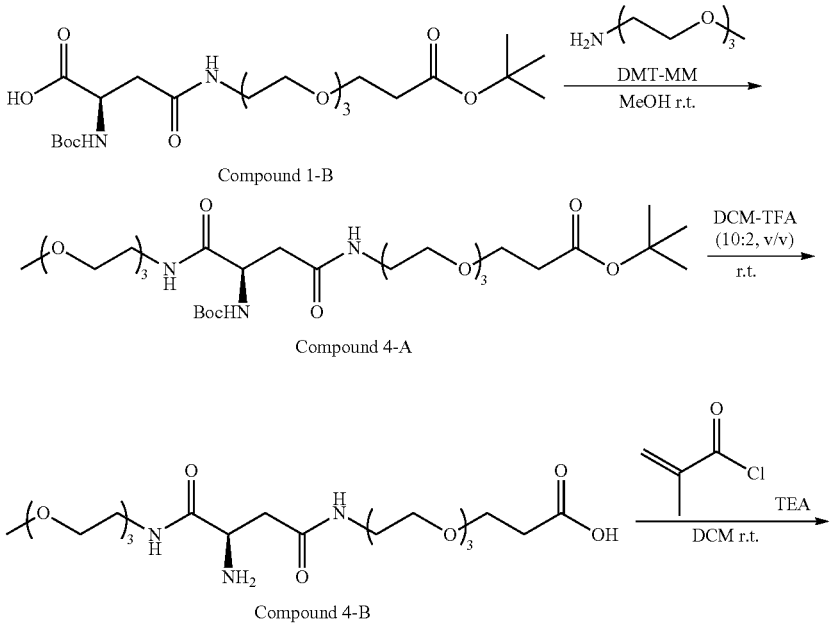

Compound 1-B

Compound 4-A

Compound 4-B

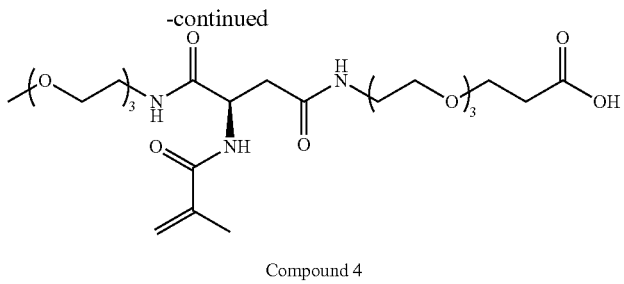

Compound 4

Synthesis of Compound 4-A

A compound 4-A was synthesized in the same manner as that used for synthesizing the compound 1-C, except that the used raw materials were changed.

Synthesis of Compound 4-B

A compound 4-B was synthesized in the same manner as that used for synthesizing the compound 1-E, except that the used raw materials were changed.

Synthesis of Compound 4

A compound 4 was synthesized in the same manner as that used for synthesizing the compound 1, except that the used raw materials were changed.

Preparation of Fluorescent-Labeled Antibody

Example 1

(Preparation of Particles)

In a 1 L three-neck flask, 0.6 g of sodium dodecyl sulfate was dissolved in 400 g of ultrapure water. The solution was heated to 85° C. under nitrogen, 30 g of styrene was then added thereto, and the mixture was stirred for 5 minutes. In another container, 1 g of potassium persulfate was dissolved in 30 g of ultrapure water. The obtained solution was put into the aforementioned three-neck flask, and the mixture was polymerized at 85° C. for 6 hours. The mixture was cooled to room temperature and then filtered through nylon mesh N-No. 230 T, thereby obtaining core particles.

Then, 30 g of the above core particles were added to a 100 mL three-neck eggplant flask and heated to 85° C. under nitrogen. Styrene (0.5 g) and the compound 1 (0.2 g) were added thereto, and the mixture was stirred for 5 minutes. In another container, 0.067 g of potassium peroxodisulfate was dissolved in 2 g of ultrapure water. The obtained solution was put into the aforementioned three-neck flask, and the mixture was polymerized at 85° C. for 6 hours. The mixture was cooled to room temperature and then filtered through nylon mesh (N-No. 230T), and the particles were washed with ultrapure water by centrifugation, thereby obtaining particles having the compound 1 (the following structure) on the surface as a polymer unit structure.

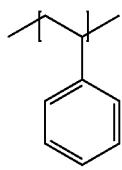

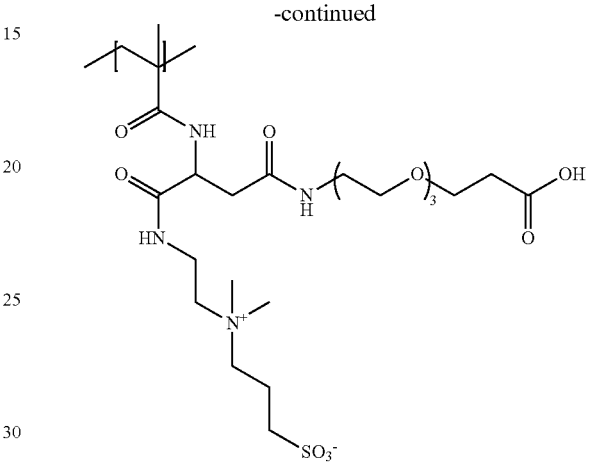

(Measurement of Carboxyl Group Content)

An aqueous dispersion (2.0 g) of the above particles having a solid content of 5% by mass was diluted with 80 g of ultrapure water, 50 μL of 1 mol/L hydrochloric acid was added thereto, and the mixture was stirred at room temperature for 5 minutes. A 0.1 mol/L aqueous sodium hydroxide solution was added dropwise thereto in a state where the electric conductivity was being measured with a pH meter HM-30R (manufactured by DKK-TOA CORPORATION). The amount of the 0.1 mol/L aqueous sodium hydroxide solution in which a carboxyl group was neutralized was measured, and from the result, the content of the carboxyl group was calculated.

(Preparation of Fluorescent Particles)

An aqueous dispersion (7.5 g) of the above particles having a solid content of 2% by mass and 1.5 mL of tetrahydrofuran were added to a 100 mL eggplant flask, and the mixture was stirred at 30° C. for 20 minutes. In another container, 0.9 mg of 3,3',5,5'-tetraphenyl-meso-aza-2,2'-dipyrromethene difluoroborate was dissolved in 0.75 mL of tetrahydrofuran, and the solution was put in the aforementioned eggplant flask, and the mixture was stirred at 30° C. for 30 minutes. Tetrahydrofuran was distilled off under reduced pressure, then the residue was filtered using a Kiriyama funnel, and the particles were washed with phosphate-buffered saline (PBS, manufactured by FUJIFILM Wako Pure Chemical Corporation) (pH 7.6) by centrifugation, thereby obtaining fluorescent particles.

(Measurement of Particle Size and Polydispersity Index of Fluorescent Particles)

An aqueous dispersion (4.0 μL) of the above fluorescent particles having a solid content of 2% by mass was diluted with 796 μL of phosphate-buffered saline (PBS, manufactured by FUJIFILM Wako Pure Chemical Corporation) (pH 7.6), and the particle size and polydispersity index of the fluorescent particles were measured using ZETASIZER NANO ZS (manufactured by Malvern Panalytical).

(Antibody Immobilization)

An aqueous dispersion (275 μL) of the above fluorescent particles having a solid content of 2% by mass was diluted with 88 μL of a 50 mmol/L 2-morpholinoethanosulfonic acid (MES, manufactured by DOJINDO LABORATORIES.) buffer (pH 5.6), 8.8 μL of an ultrapure water solution containing 10% by mass of 1-ethyl-3-(3-dimethylaminopropyl)carbodiimide hydrochloride (EDC) was added thereto, and the mixture was stirred at room temperature for 15 minutes. Then, 187 μL of 0.5 mg/mL anti-TSH monoclonal antibodies (manufactured by Meridian Life Science, Inc.: Anti-TSH Mab MAT04-410) were added thereto, and the mixture was stirred at room temperature for 1 hour so that the antibodies were immobilized onto the fluorescent particles. After immobilization, 27.5 μL of a 2 mol/L aqueous glycine solution was added thereto, and the mixture was left to stand for 15 minutes for blocking. After the reaction ended, purification was performed by centrifugation, thereby obtaining antibody-conjugated fluorescent particles.

Example 2

Antibody-conjugated fluorescent particles were obtained in the same manner as in Example 1, except that the used monomer was changed to the compound 2.

Example 3

Antibody-conjugated fluorescent particles were obtained in the same manner as in Example 1, except that the used monomer was changed to the compound 3.

Example 4

Antibody-conjugated fluorescent particles were obtained in the same manner as in Example 1, except that the used monomer was changed to the compound 4.

Comparative Example 1

(Preparation of Particles)

In a 1 L three-neck flask, 0.6 g of sodium dodecyl sulfate was dissolved in 400 g of ultrapure water. The solution was heated to 85° C. under nitrogen. Then, in a container in which 30 g of styrene was put and stirred for 5 minutes at 200 rpm, 1 g of potassium peroxodisulfate was dissolved in 30 g of ultrapure water. The obtained solution was put into the reaction container described above, and the mixture was polymerized at 85° C. for 6 hours. The mixture was cooled to room temperature and then filtered through nylon mesh N-No. 230 T, thereby obtaining core particles.

Then, 30 g of the above core particles were added to a 100 mL three-neck eggplant flask and heated to 85° C. under nitrogen. Styrene (0.25 g), 0.05 g of acrylic acid, and 0.2 g of 2-methacryloyloxyethyl phosphorylcholine (TOKYO CHEMICAL INDUSTRY CO., LTD.) were added thereto, and the mixture was stirred for 5 minutes at 200 rpm. In another container, 0.067 g of potassium peroxodisulfate was dissolved in 2 g of ultrapure water, and the solution was put in the aforementioned three-neck eggplant flask and polymerized at 85° C. for 6 hours. The mixture was cooled to room temperature and then filtered through nylon mesh (N-No. 230T), and the particles were washed with ultrapure water by centrifugation, thereby obtaining particles having a carboxyl group and a phosphorylcholine group (the following structure) on the surface as a polymer unit structure.

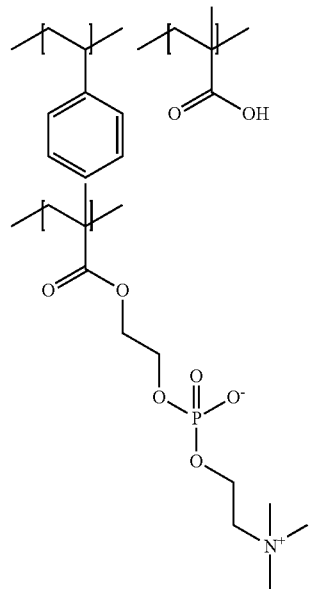

Subsequently, by using the above particles, fluorescent-labeled antibodies were obtained in the same manner as in Example 1.

<Evaluation of Antibody Binding Amount>

In the process of preparing the fluorescent-labeled antibodies of examples and comparative examples described above, antibodies contained in the supernatant obtained by centrifugation was quantified using NANODROP 2000c (manufactured by Thermo Fisher Scientific Inc.), and the amount of antibodies immobilized onto the fluorescent particles was calculated. The equation used for calculation and the evaluation standard are as below.

Antibody binding amount=(amount of antibody added (μm))−(amount of antibody in centrifugation supernatant (μm))/(particle weight (mg))

(Antibody Binding Amount)
S: Equal to or greater than 100 μg/mg
A: Equal to or greater than 80 μg/mg and less than 100 μg/mg
B: Equal to or greater than 60 μg/mg and less than 80 μg/mg
C: Equal to or greater than 40 μg/mg and less than 60 μg/mg
D: Less than 40 μg/mg <Evaluation of Non-Specific Adsorption Inhibitory Effect>

An aqueous dispersion (500 μL) of the fluorescent particles obtained in each of the above examples and comparative examples having a solid content of 2% by mass was diluted with 500 μL of PBS. The dispersion was centrifuged, 950 μL of supernatant was removed, and then 950 μL of bovine serum albumin (BSA, FUJIFILM Wako Pure Chemical Corporation) in a PBS solution (1 mg/mL) was added thereto. Redispersion was performed using ultrasonic waves, and then the dispersion was stirred at room temperature for 2 hours so that BSA was adsorbed onto the fluorescent particles. The dispersion was stirred and then centrifuged, BSA contained in the supernatant was quantified using NANODROP 2000c (manufactured by Thermo Fisher Scientific Inc.), and the amount of BSA non-specifically adsorbed onto the fluorescent particles was calculated. The equation used for calculation and the evaluation standard are as below.

Non-specific adsorption amount=(amount of BSA added (µg))−(amount of BSA in centrifugation supernatant (m))/(particle weight (mg))

(Non-Specific Adsorption Amount)

S: Less than 10 µg/mg

A: Equal to or greater than 10 µg/mg and less than 20 µg/mg

B: Equal to or greater than 20 µg/mg and less than 30 µg/mg

C: Equal to or greater than 30 µg/mg and less than 40 µg/mg

D: Equal to or greater than 40 µg/mg

<TSH Evaluation by Sandwich Method>

By using the above fluorescent-labeled antibodies, thyroid stimulating hormone (TSH) in a biosample was measured through fluorescence detection by surface plasmon resonance.

TSH quantification method will be described below. Substances other than TSH can also be quantified by the same method. First, a biosample being likely to contain TSH and the fluorescent-labeled anti-TSH antibody 2 are brought into contact with a TSH immunoassay substrate onto which the anti-TSH monoclonal antibody 1 is immobilized. In a case where the biosample contains TSH, by TSH which has undergone an antigen-antibody reaction with the anti-TSH antibody 2 labeled with fluorescence in advance and the anti-TSH antibody 1 on the substrate, an antigen-antibody reaction occurs on the substrate. On the other hand, in a case where the biosample does not contain TSH, no antigen-antibody reaction occurs between the fluorescent-labeled anti-TSH antibody 2 mixed with the biosample and the anti-TSH antibody 1 on the substrate. After the above reaction ends, the fluorescent-labeled anti-TSH antibody 2 that did not bind to the anti-TSH antibody 1 on the substrate is removed. Then, the degree of formation of an immune complex on the substrate (that is, a complex of the fluorescent-labeled anti-TSH antibody 2, TSH, and the anti-TSH antibody 1 on the substrate) is detected as fluorescence intensity.

(Preparation of Substrate)

A polymethylmethacrylate (PMMA) substrate (Acrypet (registered trademark) VH manufactured by Mitsubishi Rayon Co., Ltd.) was prepared, and a gold film having a thickness of 45 nm was prepared on one surface of the substrate by a sputtering method. The substrate was cut in a width of 7 mm, thereby preparing the same seven substrates. A solution (concentration: 10 µg/mL in 150 mmol/L NaCl) containing the prepared anti-TSH monoclonal antibody 1 (manufactured by Medix Inc., 5409) was dispensed on the gold film surface of each of the substrates and dried, thereby obtaining substrates onto which the anti-TSH antibody was immobilized. A PBS solution (pH 7.4) containing Tween 20 (polyoxyethylene (20) sorbitan monolaurate (manufactured by FUJIFILM Wako Pure Chemical Corporation)) at a concentration of 0.05% by mass was prepared in advance, and the prepared substrates were repeatedly washed 3 times with 300 µL of the solution. After the washing ended, in order to block the portion of the gold film surface onto which the anti-TSH antibody was not adsorbed, 300 µL of a PBS solution (pH 7.4) containing 1% by mass of casein (manufactured by Thermo Fisher Scientific Inc.) was added to the substrates, and the substrates were left to stand for 1 hour at room temperature. The substrates were washed with the washing solution described above, 300 µL of Immunoassay Stabilizer (manufactured by Advanced Biotechnologies, Inc.) was added thereto as a stabilizer, and the substrates were left to stand at room temperature or 30 minutes. The solution was removed, and water was completely removed using a dryer, thereby preparing substrates for evaluation.

(Preparation of Sensor Chip)

Figure 2:
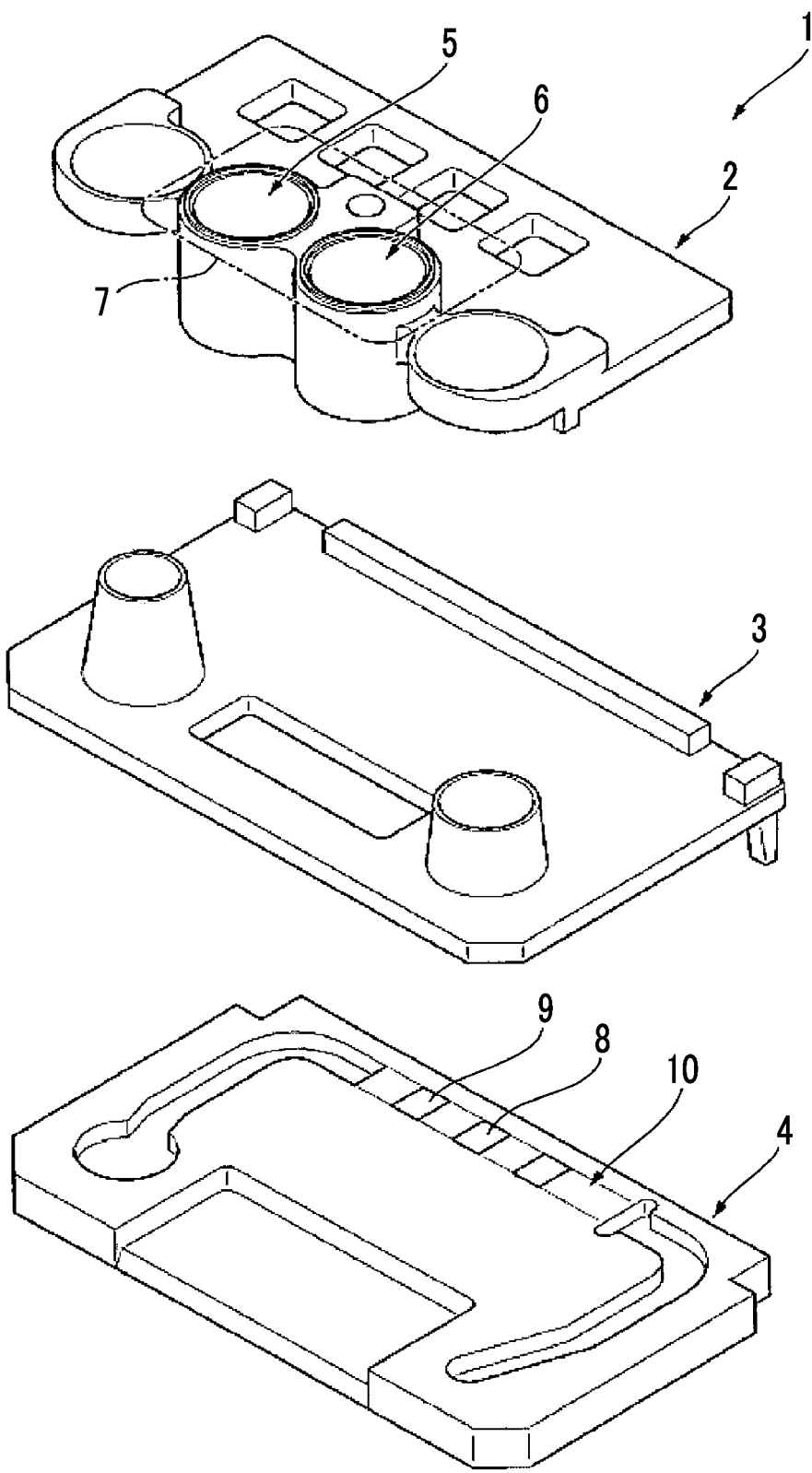
FIG. 2 is an exploded view of the sensor chip 1.

A flow channel-type sensor chip constituted as described in the second embodiment of JP2010-190880A was prepared. FIGS. 1 and 2 schematically show the sensor chip. FIG. 1 is a schematic view of a sensor chip 1, and FIG. 2 is an exploded view of the sensor chip 1. The sensor chip 1 is constituted with an upper member 2, an intermediate member 3, and a substrate 4. The upper member 2 is provided with a first container 5 and a second container 6. The first container 5 and the second container 6 are collectively called container group 7. A flow channel 10 is formed on the substrate 4, and a detection area 8 and a reference area 9 are formed on the flow channel 10.

(Preparation of Test Sample)

As test samples, dog sera having TSH concentrations of about 0 ng/mL and about 0.4 ng/mL were used. The prepared dog sera were oriental beagle sera purchased from KITAYAMA LABES CO., LTD.

(Tsh Evaluation)

By using the fluorescent-labeled antibodies prepared as above, TSH was measured with IMMUNO AU10V (manufactured by FUJIFILM Corporation). Mixed solutions of 100 µL of each of the test samples (dog sera) prepared as above and the fluorescent-labeled anti-TSH antibodies were prepared and stirred for 10 minutes. Then, each of the mixed solutions of the fluorescent-labeled antibodies and the test sample was dispensed in the flow channel-type sensor chip in which the substrate prepared as above was enclosed. After the dispensing, aspiration was performed using a pump. In this state, the mixed solution was allowed to flow down at a rate of 10 µL/min so that the solution was brought into contact with the gold film surface onto which the anti-TSH antibody was immobilized, and fluorescence intensity was continuously measured for 1.5 minutes. The rate of increase of the fluorescence intensity per unit time obtained in the substrate was determined. From the rate of increase obtained from two test samples, S/N was calculated, and relative S/N was compared. The equation used for calculation and the evaluation standard are as below.

S/N=(rate of increase obtained from test sample with TSH concentration of about 0.4 ng/mL)/(rate of increase obtained from test sample with TSH concentration of about 0 ng/mL)

Relative S/N=(S/N of each of examples and comparative examples)/(S/N of Comparative Example 1)

(Relative S/N)

S: Equal to or higher than 2.0

A: Equal to or higher than 1.7 and less than 2.0

B: Equal to or higher than 1.4 and less than 1.7

C: Equal to or higher than 1.1 and less than 1.4

D: Less than 1.1

TABLE 1

| | Amount of carboxyl group (µmol/g) | Particle size (nm) | Poly-disperity index | Antibody binding amount | Non-specific adsorption inhibitory effect | Relative S/N |
|---|---|---|---|---|---|---|
| Example 1 | 186 | 152 | 0.053 | S | A | A |
| Example 2 | 170 | 153 | 0.063 | S | A | S |
| Example 3 | 192 | 158 | 0.049 | B | S | B |
| Example 4 | 178 | 152 | 0.030 | A | B | C |
| Comparative Example 1 | 90 | 162 | 0.054 | D | C | D |

It has been revealed that in a case where Example 1 or Example 2 of the present invention is used, a high antibody binding amount and a high non-specific adsorption inhibitory effect can be simultaneously achieved, and a test sample can be detected with high sensitivity.

EXPLANATION OF REFERENCES

1: sensor chip
2: upper member
3: intermediate member
4: substrate
5: first container
6: second container
7: container group
8: detection area
9: reference area
10: flow channel

What is claimed is:

1. A solid phase carrier for carrying a bioactive substance, comprising:
   a copolymer of a structural unit represented by Formula (1) and a styrene,
   wherein the copolymer is present on a surface of the solid phase carrier,

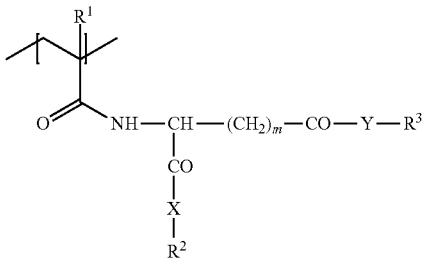

(1)

in the formula, $R^1$ represents a hydrogen atom or a methyl group;
X represents —NH— or —O—;
Y represents —NH— or —O—;
m represents an integer from 1 to 5; and
wherein $R^2$ represents a hydrophilic group and $R^3$ represents a group represented by Formula (R-1) or wherein $R^3$ represents a hydrophilic group and $R^2$ represents a group represented by Formula (R-1),

(R-1)

n represents an integer of 1 to 12, $R^4$ represents a bioactive substance-reactive group, and * represents a position bonded to X or Y.

2. The solid phase carrier according to claim 1, wherein X is —NH—, and Y is —NH—.
3. The solid phase carrier according to claim 1, wherein m is 1 or 2.
4. The solid phase carrier according to claim 1, wherein the hydrophilic group has a betaine structure, a sugar structure, an amino acid structure, or a sulfonic acid group.
5. The solid phase carrier according to claim 1, wherein the bioactive substance-reactive group has a carboxyl group, an active ester, an isothiocyanate, an epoxy group, or a maleimide.
6. The solid phase carrier according to claim 1, wherein n in Formula (R-1) is an integer of 3 to 6.
7. The solid phase carrier according to claim 1, wherein a content of the bioactive substance-reactive group is 1 to 500 µmol per 1 g of a solid content of the solid phase carrier.
8. The solid phase carrier according to claim 1, wherein the solid phase carrier is in the form of a particle.
9. The solid phase carrier according to claim 8, wherein the particle has a particle size of 50 to 300 nm.
10. The solid phase carrier according to claim 8, wherein a polydispersity index of the particle size of the particle is equal to or higher than 0.002 and equal to or lower than 0.10.
11. The solid phase carrier according to claim 8, wherein the particle contains a fluorescent dye.
12. The solid phase carrier according to claim 11, wherein the fluorescent dye is an azadipyrromethene dye or a dipyrromethene dye.
13. The solid phase carrier according to claim 1, wherein a bioactive substance is bonded to the bioactive substance-reactive group represented by $R^4$.
14. The solid phase carrier according to claim 13, wherein the bioactive substance is an antibody.
15. A kit for measuring a measurement target substance in a biosample, comprising:
   the solid phase carrier according to claim 1; and
   a substrate having a detection area on a metal film.

* * * * *